(12) United States Patent
Habicht et al.

(10) Patent No.: US 11,304,443 B2
(45) Date of Patent: Apr. 19, 2022

(54) VAPORIZER HEATING ASSEMBLY

(71) Applicant: SV3, LLC, Phoenix, AZ (US)

(72) Inventors: Geoff Habicht, Phoenix, AZ (US); Amir Hakak, Phoenix, AZ (US)

(73) Assignee: SV3, LLC, Phoenix, AZ (US)

( * ) Notice: Subject to any disclaimer, the term of this patent is extended or adjusted under 35 U.S.C. 154(b) by 582 days.

(21) Appl. No.: 16/052,413

(22) Filed: Aug. 1, 2018

(65) Prior Publication Data

US 2019/0037924 A1    Feb. 7, 2019

Related U.S. Application Data

(60) Provisional application No. 62/539,939, filed on Aug. 1, 2018.

(51) Int. Cl.

| | |
|---|---|
| *A24F 1/24* | (2006.01) |
| *A61M 15/06* | (2006.01) |
| *A24F 40/42* | (2020.01) |
| *A24F 40/46* | (2020.01) |
| *A61M 11/04* | (2006.01) |

(52) U.S. Cl.
CPC ............ *A24F 1/24* (2013.01); *A24F 40/42* (2020.01); *A24F 40/46* (2020.01); *A61M 15/06* (2013.01); *A61M 11/042* (2014.02); *A61M 2205/505* (2013.01); *A61M 2205/8206* (2013.01); *H05B 2203/021* (2013.01)

(58) Field of Classification Search
None
See application file for complete search history.

(56) References Cited

U.S. PATENT DOCUMENTS 10,462,849 B1 * 10/2019 Reichert ............... A24F 47/008
2016/0174611 A1 * 6/2016 Monsees ................ H05B 3/04
392/387

* cited by examiner

*Primary Examiner* — Phu H Nguyen
(74) *Attorney, Agent, or Firm* — Snell & Wilmer L.L.P.

(57) ABSTRACT

A vaporizer heating element is disclosed. In various embodiments, the vaporizer heating element comprises a heat conductor embedded within a cup. The cup defines a chamber configured to receive tobacco and/or other plant-based extracts. The heat conductor is configured to receive an electrical current and increase a temperature of the cup.

20 Claims, 3 Drawing Sheets

VAPORIZER HEATING ASSEMBLY

CROSS REFERENCE TO RELATED APPLICATION

This non-provisional patent application claims priority to U.S. Provisional Patent Application No. 62/539,938, filed on Aug. 1, 2017, entitled "VAPORIZER HEATING ELEMENT," which is incorporated herein by reference in its entirety.

FIELD OF THE INVENTION

The present invention elates to vaporizers and in particular to a vaporizer heating assembly having a cup and integrated heat conductor.

BACKGROUND OF THE INVENTION

Vaporizers are typically used to aerosolize liquids or volatile substances contained in solid or semisolid substances. Vaporizers designed for tobacco, dried plant materials, and other plant-based extracts or oils have recently grown in popularity as people move aware from harmful cigarettes to safer electronic devices. To operate these devices, a user must typically place the plant material, extract, or oil to be vaporized directly onto a ceramic or glass rod piece, which may be wrapped in a heat-conductive wire. In such systems, some plant material, extract, or oil may gather beneath the ceramic piece. Additionally, plant material, extract, or oil may be placed in direct contact with the heat-conductive wire, exposing it to high temperatures and causing it to burn rather than vaporize. Burning plant material, extract, or oil may cause the user to inhale various irritants or carcinogens, and may negatively affect the flavor of the inhaled vapor. Moreover, because the plant material, extract, or oil may melt and solidify around and under the heat-conductive wire and the ceramic or glass rod piece, the vaporizer may be difficult to clean, further negatively affecting the inhalant's flavor and the vaporizer's efficacy during future use. Accordingly, new and improved vaporizers are needed.

SUMMARY

In various exemplary embodiments the present invention is directed to a vaporizer comprising a battery in electrical communication with a vaporizer heating assembly, and a mouthpiece in fluid communication with the vaporizer heating assembly, wherein the vaporizer heating assembly comprises a heat conductor at least partially embedded within a cup, the heat conductor comprising a first end and a second end, wherein the cup comprises an interior surface that defines a chamber, wherein at least one of the first end and the second end is configured to receive an electrical current, and wherein the heat conductor is configured to increase a temperature of the interior surface of the cup.

In various embodiments, the heat conductor further comprises a coil completely embedded within a bottom side of the cup, and at least one of the first end and the second end extends outwardly from an exterior surface of the cup. In various embodiments, the vaporizer further comprises an electrical connector coupled to at least one of the first end and the second end. In various embodiments, the electrical connector comprises a 510 electrical connector. In various embodiments, the vaporizer further comprises a cover coupled to, and at least partially surrounding, the exterior surface of the cup. In various embodiments, in response to communication of an electrical current through the heat conductor, the interior surface of the cup comprises a temperature of 250° F. to 650° F. In various embodiments, the cup comprises quartz. In various embodiments, the heat conductor comprises a wire. In various embodiments, the interior surface of the cup comprises at least one of curved, beveled, or chamfered interior edges.

In various exemplary embodiments, the present invention is directed to a vaporizer heating assembly comprising a heat conductor at least partially embedded within a cup, the heat conductor comprising a first end and a second end, wherein the cup comprises an interior surface that defines a chamber, wherein at least one of the first end and the second end is configured to receive an electrical current, and wherein the heat conductor is configured to increase a temperature of the interior surface of the cup.

In various embodiments, the heat conductor further comprises a coil completely embedded within a bottom side of the cup, and at least one of the first end and the second end extends outwardly from an exterior surface of the cup. In various embodiments, the vaporizer heating assembly further comprises an electrical connector coupled to at least one of the first end and the second end. In various embodiments, the electrical connector comprises a 510 electrical connector. In various embodiments, the vaporizer heating assembly further comprises a cover coupled to, and at least partially surrounding, the exterior surface of the cup. In various embodiments, in response to communication of an electrical current through the heat conductor, the interior surface of the cup comprises a temperature of 250° F. to 650° F. In various embodiments, the cup comprises quartz. In various embodiments, the heat conductor comprises a wire. In various embodiments, the interior surface of the cup comprises at least one of curved, beveled, or chamfered interior edges.

In various exemplary embodiments, the present invention is directed to a vaporizer heating assembly, comprising a quartz cup comprising an interior surface and an exterior surface, wherein the interior surface comprises at least one of curved, beveled, or chamfered interior edges and the exterior surface is surrounded by a cover, a heat conductor comprising a wire coil, a first end, and a second end, wherein the wire coil is completely embedded in a bottom side of the cup and at least one of the first end and the second end extend outward from the exterior surface of the cup, and an electrical connector coupled to, and in electrical communication with, at least one of the first end and the second end, wherein the electrical connector is configured to communicate an electrical current from a battery to the heat conductor. In various embodiments, in response to communication of an electrical current through the heat conductor, the interior surface of the cup comprises a temperature of 250° F. to 650° F.

BRIEF DESCRIPTION OF THE DRAWINGS

The accompanying drawings are included to provide a further understanding of the present disclosure and are incorporated in, and constitute a part of, this specification, illustrate various embodiments, and together with the description, serve to explain the principles of the disclosure.

DETAILED DESCRIPTION OF THE INVENTION

Figure 1A:
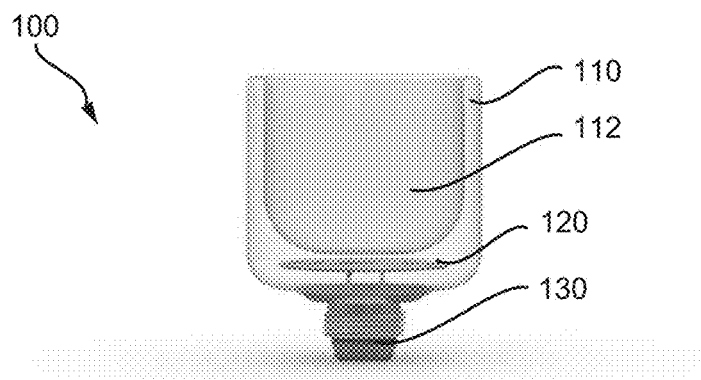
FIGS. 1a-1c illustrate perspective views of a vaporizer heating assembly in accordance with various embodiments.

The following description is of various embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the present disclosure or appended claims.

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and/or functional changes may be made without departing from the spirit and scope of the disclosure. Thus, the detailed description herein is presented for purposes of illustration only and not of limitation. Any reference to singular includes plural embodiments, and any reference to more than one component may include a singular embodiment.

Vaporizer systems and devices are provided. In the detailed description herein, references to "an exemplary embodiment," "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

For the sake of brevity, conventional vaporizers and vaporizer components may not be described in detail herein. Furthermore, the connecting lines shown in various figures contained herein are intended to represent exemplary functional relationships and/or physical or communicative couplings between various elements. It should be noted that many alternative or additional functional relationships or physical or communicative connections may be present in a practical vaporizer system.

In various embodiments, a vaporizer heating assembly is disclosed herein. The vaporizer heating assembly may be configured to heat tobacco or other plant materials, extracts, or oils at a temperature such that volatile substances contained in the tobacco or other plant material, extract, or oil are vaporized without combustion. In various embodiments, the vaporizer heating assembly may be compatible for use in a portable vaporizer, vaporizer pen, desktop vaporizer, or any other suitable type of vaporizer.

Figure 1B:
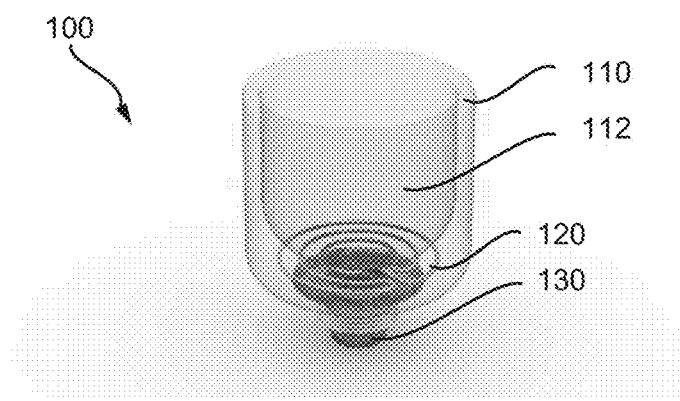
Figure 1C:
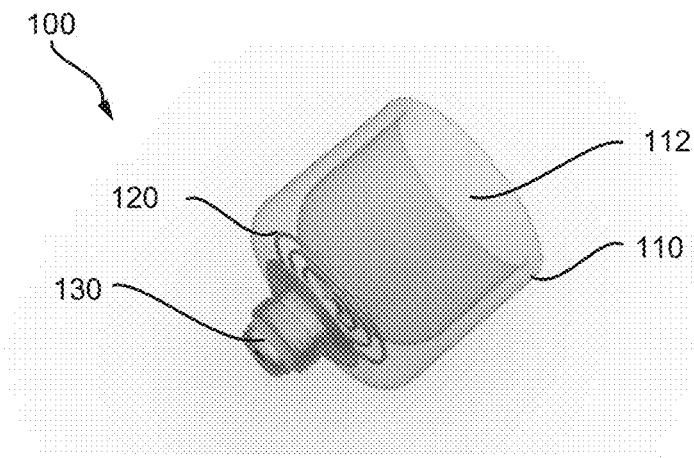

In various embodiments and with reference to FIGS. 1a-1c, a vaporizer heating assembly 100 comprises a cup 110. In various embodiments, cup 110 defines a chamber 112 that is partially enclosed by cup 110. A top edge of cup 110 defines an aperture or opening through which chamber 112 may be accessed. Cup 110 and/or chamber 112 may be configured to receive tobacco or a plant material, extract, or oil. In various embodiments, cup 110 comprises an exterior surface having a cylindrical shape and an interior surface that defines a generally cylindrical chamber 112. However, the exterior surface of the cup may comprise a conical, spherical, cuboid, prismatic, or any other exterior shape suitable for use in vaporizer heating assembly 100. Similarly, the interior surface of the cup may define a chamber having a conical, spherical, cuboid, prismatic, or any other shape suitable for use in vaporizer heating assembly 100. In various embodiments, the shape of cup 110 is compatible with the vaporizer to which it is coupled.

In various embodiments, the shape of chamber 112 is configured to be easily cleaned after usage. The shape of chamber 112 and/or the interior surface of the cup 110 may lack corners, edges, channels, divots, apertures, and/or bores from which tobacco or plant material, extract, or oil are difficult to remove. Chamber 112 and/or the interior surface of the cup 110 may comprise one or more curved surfaces. Chamber 112 and/or the interior surface of the cup 110 may comprise one or more beveled edges, one or more interior chamfered edges, and/or any other surface suitable for use in vaporizer heating assembly 100.

In various embodiments, cup 110 comprises a heat conductive material. Cup 110 may comprise a material suitable to apply heat to tobacco or plant material, extract, or oil placed within chamber 112 at a uniform temperature across the interior surface of the cup 110 and/or chamber 112. Cup 110 may comprise a material that is smooth, scratch or dent resistant, lubricating, repelling, and/or otherwise has characteristics that make the interior surface of cup 110 easy to clean. In various embodiments, cup 110 comprises quartz. In various embodiments, cup 110 comprises borosilicate glass, soda-lime glass, or any other suitable type of glass. However, cup 110 may comprise any mineral, metal, alloy, ceramic, composite, or other material suitable for use in vaporizer heating assembly 100.

Figure 3:
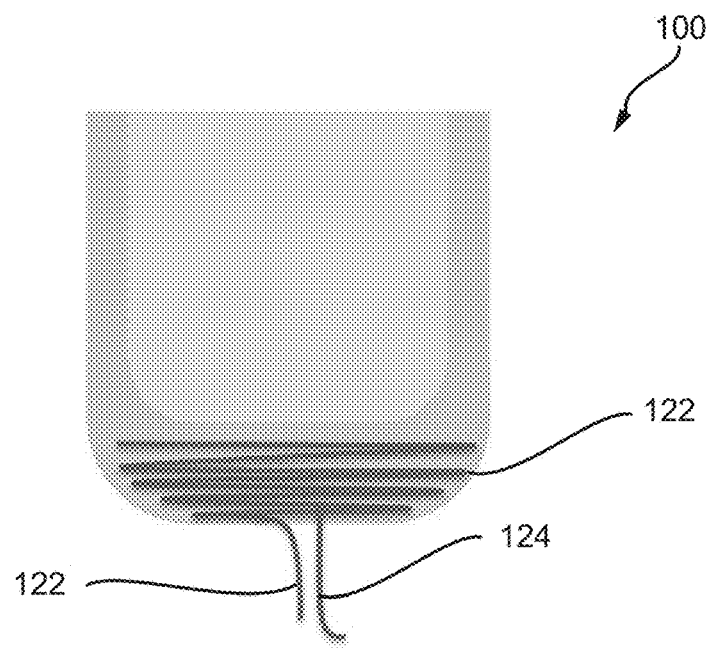
FIG. 3 illustrates a cross section view of a vaporizer heating assembly in accordance with various embodiments.

In various embodiments, vaporizer heating assembly 100 further comprises a heat conductor 120. Heat conductor 120 may be configured to receive an electrical current from a power source, such as a battery, electric socket, electric generator, or the like. Heat conductor 120 may be configured to transfer heat to cup 110. In various embodiments, heat conductor 120 is at least partially embedded within a bottom side of cup 110. As used herein, the bottom side of cup 110 should be understood to be the portion of cup 110 disposed generally opposite of the aperture or opening defined by the top edge of cup 110. In various embodiments and with momentary reference to FIG. 3, a coil 122 of heat conductor 120 is fully embedded within the bottom side of cup 110 and one or more ends 124 of heat conductor 120 extend outwardly from the exterior surface of cup 110 and/or below the bottom side of cup 110. However, heat conductor 120 may be embedded within any side and/or other portion of cup 110 suitable for providing even heat distribution to the interior surface of cup 110 and/or chamber 112.

In various embodiments and with reference again to FIGS. 1a-1c, heat conductor 120 comprises a wire. In various embodiments, the length of the wire is determined by the size and/or shape of cup 110. The length of the wire may be the maximum length capable of being embedded within the bottom side of cup 110. In various embodiments, and with momentary reference to FIG. 3, the wire may be oriented within the bottom side of cup 110 to form a coil 122. However, the wire may be oriented within the bottom side of the cup to form a zig-zag pattern, hairpin pattern, or any other pattern suitable for embedding the wire in the cup.

Heat conductor 120 may comprise a diameter of between about 3.26 mm and about 0.07 mm (8 gauge to 40 gauge). Heat conductor 120 may comprise a 26 gauge wire. Heat conductor 120 may comprise a diameter of about 0.40 mm. However, heat conductor 120 may comprise any diameter suitable for being embedded in cup 110.

Heat conductor 120 may comprise a metal such as titanium, copper, tungsten, aluminum, gold, or nickel. Heat conductor 120 may comprise a metal alloy such as a nickel-chromium alloy, iron-chromium-aluminum alloy, stainless steel, zinc alloy, or any other suitable alloy including commercially-available alloys such as Kanthal® wire produced by the Bulten-Kanthal company of Hallstahammar, Sweden. However heat conductor 120 may comprise any mineral, metal, alloy, ceramic, composite, or other material suitable for use in vaporizer heating assembly 100. In various embodiments, heat conductor 120 may be selected based on physical properties of cup 110. For example, heat conductor 120 may comprise a material having a maximum temperature threshold (based on the voltage applied to it by a power source) below a melting temperature of cup 110.

In various embodiments, heat conductor 120 may be configured to receive a voltage of between about 1.5V and about 8V. More preferably, heat conductor 120 may be configured to receive a voltage of between about 2V and about 5V. In various embodiments, heat conductor 120 is configured to receive a voltage of about 2.5V to about 3V when the heating assembly is used with dried plant materials. In various embodiments, heat conductor 120 is configured to receive a voltage of about 3V to about 4V when the heating assembly is used with concentrated plant extracts, including waxes, shatters, crumbles, dabs, resins, or other concentrates. In various embodiments, heat conductor 120 is configured to receive a voltage of about 2.5V to about 3.5V when the heating assembly is used with plant-based oils. However, heat conductor 120 may receive any voltage suitable for providing heat to cup 110.

Figure 2A:
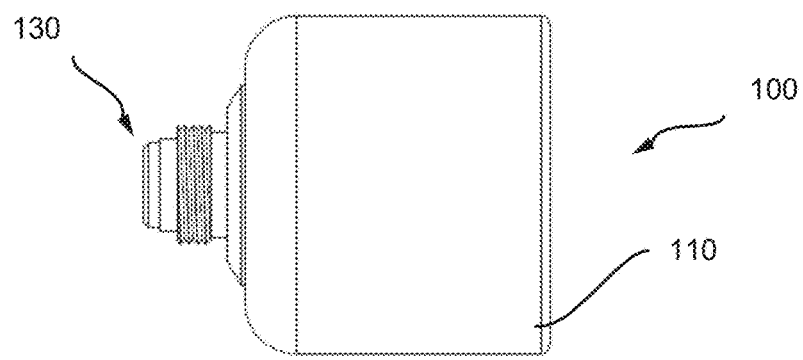
FIGS. 2a and 2b illustrate perspective views of a vaporizer heating assembly in accordance with various embodiments.
Figure 2B:
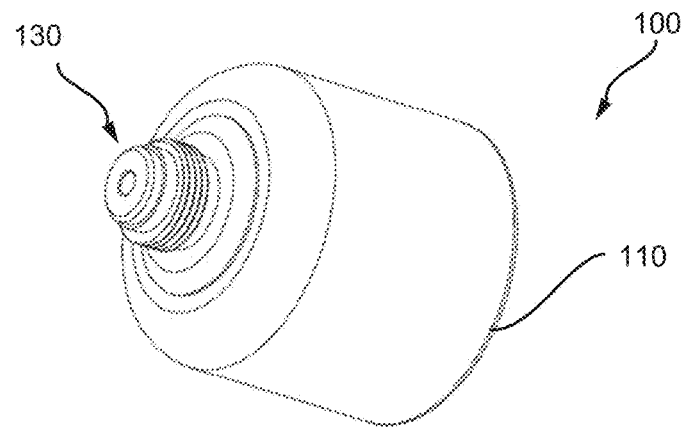
Figure 2C:
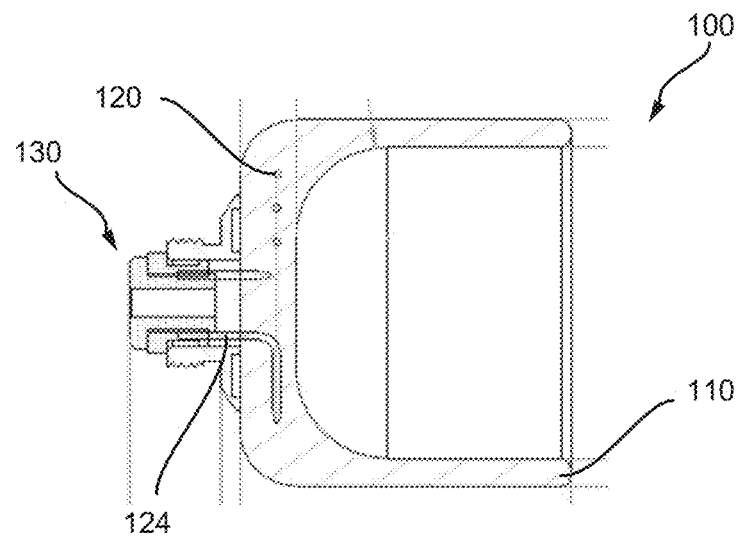
FIG. 2c illustrates a cross section view of a vaporizer heating assembly in accordance with various embodiments.

In various embodiments and with reference to FIGS. 2a-2c, heat conductor 120 is coupled to electrical connector 130. In various embodiments, electrical connector 130 is mechanically and/or electrically coupled to one or more ends 124 of heat conductor 120. Electrical connector 130 may be configured to communicate a current from a power source to heat conductor 120. In various embodiments, electrical connector 130 comprises a 510 thread connector. However, electrical connector 130 may comprises an 808 thread connector, an eGo™ connector, or any other electrical connector suitable to communicate an electrical current from a power source to heat conductor 120.

In various embodiments, heat conductor 120, electrical connector 130, and/or cup 110 are configured to heat chamber 112 to between about 190° F. and about 800° F. More preferably, heat conductor 120, electrical connector 130, and/or cup 110 may be configured to heat chamber 112 to between about 300° F. and about 600° F., Heat conductor 120, electrical connector 130, and/or cup 110 may be configured to heat chamber 112 to between about 300° F. and about 400° F. Heat conductor 120, electrical connector 130, and/or cup 110 may be configured to heat chamber 112 to between about 400° F. and about 500° F. Heat conductor 120, electrical connector 130, and/or cup 110 may be configured to heat chamber 112 to between about 500° F. and about 600° F.

The resistance of heat conductor 120, the voltage provided through electrical connector 130, and/or the heat conductive properties of cup 110 and heat conductor 120 may be optimized and/or varied to heat chamber 112 to a desired temperature. In various embodiments, electrical connector 130, heat conductor 120, and/or cup 110 may be configured to heat chamber 112 to between about 270° F. and about 450° F. when the heating assembly is used with dried plant materials. In various embodiments, electrical connector 130, heat conductor 120, and/or cup 110 may be configured to heat chamber 112 to between about 400° F. and about 650° F. when the heating assembly is used with concentrated plant extracts, including waxes, shatters, crumbles, dabs, resins, or other concentrates. In various embodiments, electrical connector 130, heat conductor 120, and/or cup 110 may be configured to heat chamber 112 to between about 350° F. and about 550° F. when the heating assembly is used with plant-based oils. However, heat conductor 120 may receive any voltage suitable for providing heat to cup 110.

Figure 4:
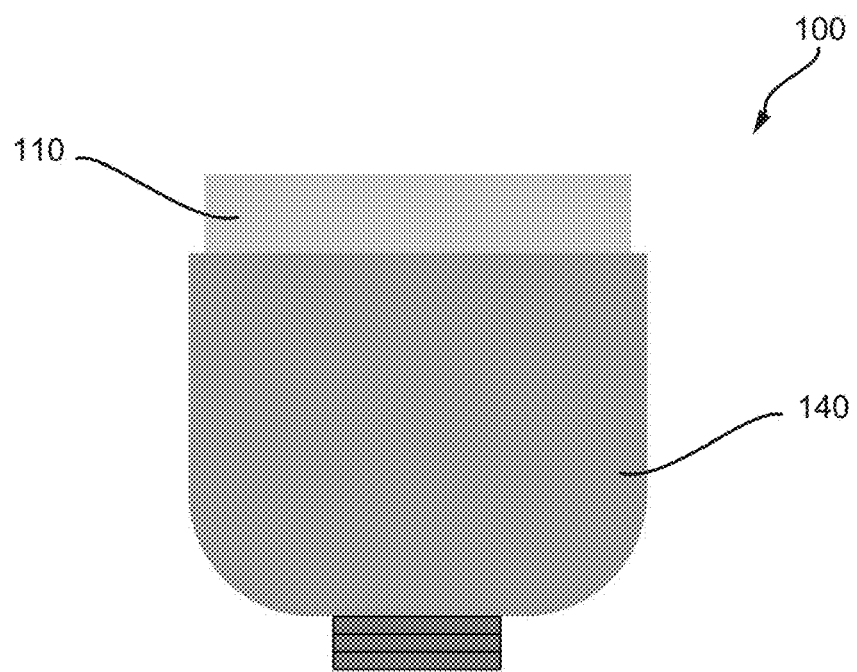
FIG. 4 illustrates a perspective view of a vaporizer heating assembly in accordance with various embodiments.

In various embodiments and with reference to FIG. 4, vaporizer heating assembly 100 may further comprise a cover 140. Cover 140 may be coupled to and/or disposed on an exterior surface of cup 110. Cover 140 may be configured to at least partially surround the exterior surface of cup 110. Cover 140 may be configured to electrically and/or thermally insulate cup 110. Cover 140 may be configured to prevent direct contact between cup 110 and a user. In various embodiments, cover 140 comprises an insulating material such as polystyrene, polyurethane, silicone, or any other insulating material suitable for use in vaporizer heating assembly 100. In various embodiments, cover 140 comprises aluminum, stainless steel, zinc alloy, silicone, or any other suitable metal, metal alloy, composite, ceramic, plastic, or rubber.

In various embodiments, a vaporizer heating assembly as described herein may be disposed in a vaporizer. The vaporizer may comprise a housing configured to partially or completely enclose the vaporizer heating assembly. In various embodiments, the vaporizer further comprises a power source, such as a battery. In various embodiments, the battery comprises a lithium ion battery. In various embodiments, the battery is rechargeable. However, the battery may comprise an alkaline battery, nickel metal hydride battery, nickel cadmium battery, or any other suitable battery. In various embodiments, the battery comprises between about 200 mAh and about 5000 mAh. However, the battery may comprise any suitable capacity. In various embodiments, the battery is configured to deliver a voltage of between about 2V and about 5V.

The battery may be disposed at least partially within the housing. The battery may be mechanically and/or electrically coupled to vaporizer heating assembly 100. The battery may be directly coupled to a first end and/or a second end of heat conductor 120. The battery may be indirectly coupled to heat conductor 120 via one or more intervening components of the vaporizer and/or the vaporizer heating assembly 100.

In various embodiments, the battery may be in communication with a controller disposed within the housing. The controller may comprise a programmable circuit board. The controller may comprise a processor configured to implement various logical operations in response to execution of instructions, for example, instructions stored on a non-transitory, tangible, computer-readable medium. In various embodiments, the controller may be configured to calculate an anticipated chamber temperature based on certain variable and non-variable inputs. Variable inputs may include a voltage applied by the power source. Non-variable inputs may include the cup material, the heat conductor material, the heat conductor length, the heat conductor gauge, the chamber volume, and/or other dimensions of the interior surface of the cup.

In various embodiments, the vaporizer may be configured to receive an input or selection from a user. The input or selection may be made by the user's manipulation of a button, touch screen, scroll, switch, or other input mechanism disposed on the vaporizer housing. In various embodiments, the user may select a desired setting. The desired setting may comprise a desired voltage to be applied by the power source and/or a desired temperature and/or temperature range to which cup 110 and/or chamber 112 will be heated. In various embodiments, in response to input or selection of a desired setting by a user, the controller causes the battery to apply, to heat conductor 120, a voltage corresponding to the desired setting.

In various embodiments, the heat conductive properties of cup 110 and heat conductor 120 may be optimized to heat chamber 112 to a desired temperature more quickly than conventional vaporizers. In various embodiments, cup 110 reaches a temperature of between about 250° F. and about 650° F. in less than thirty seconds after the user has input the desired setting. In various embodiments, cup 110 reaches a temperature of between about 250° F. and about 650° F. in between about 10 second and about 15 second after the user has input the desired setting.

In various embodiments, the vaporizer comprises a pre-heat setting. Selection of the pre-heat setting by a user may cause controller to cause application of less than about 2V to heat conductor 120. The pre-heat setting may allow a user to heat, but not vaporize, plant materials, extracts, or oils disposed in cup 110. The pre-heat setting may facilitate or improve a user's ability to clean cup 110.

In various embodiments, the vaporizer may further comprise a mouthpiece. The mouthpiece may be coupled to and/or disposed at least partially within the housing, in various embodiments, the mouthpiece comprises a contact portion that is configured to be in contact with a user's mouth and is disposed distally from a coupling portion that is coupled to the vaporizer. A vapor channel may be disposed between the contact portion and the coupling portion. The vapor channel may comprise a channel, tube, hollow cylinder, hose, or other conduit configured to bring a portion of the vaporizer heating assembly into fluid communication with the contact portion and the mouth of a user. In various embodiments, the vapor channel is configured to bring the chamber of the vaporizer heating assembly into fluid communication with the contact portion and the mouth of a user. In various embodiments, the mouthpiece comprises at least one of glass, silicone, metal, plastic, composite, or any other material suitable for use in the vaporizer.

It will be apparent to those skilled in the art that various modifications and variations can be made to the present disclosure without departing from the spirit or scope of the disclosure. Thus, it is intended that the present disclosure cover the modifications and variations of this disclosure provided they come within the scope of the appended claims and their equivalents.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all of the claims.

It should be understood that the detailed description and specific examples, indicating exemplary embodiments, are given for purposes of illustration only and not as limitations. Many changes and modifications may be made without departing from the spirit thereof, and principles of the present disclosure include all such modifications. Corresponding structures, materials, acts, and equivalents of all elements are intended to include any structure, material, or acts for performing the functions in combination with other elements. Reference to an element in the singular is not intended to mean "one and only one" unless explicitly so stated, but rather "one or more." Moreover, when a phrase similar to "at least one of A, B, or C" or "at least one of A, B, and C" is used in the claims or the specification, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A vaporizer comprising:
   a battery in electrical communication with a vaporizer heating assembly; and
   a mouthpiece in fluid communication with the vaporizer heating assembly, wherein the vaporizer heating assembly comprises:
   a heat conductor at least partially embedded within a cup, the heat conductor comprising a first end and a second end,
   wherein the cup comprises an interior surface that defines a chamber,
   wherein at least one of the first end and the second end is configured to receive an electrical current, and
   wherein the heat conductor is configured to increase a temperature of the interior surface of the cup.

2. The vaporizer of claim 1, wherein the heat conductor further comprises a coil embedded within a bottom side of the cup, and wherein at least one of the first end and the second end extends outwardly from an exterior surface of the cup.

3. The vaporizer of claim 2, further comprising an electrical connector coupled to at least one of the first end and the second end.

4. The vaporizer of claim 3, wherein the electrical connector comprises a 510 thread connector.

5. The vaporizer of claim 3, further comprising a cover coupled to, and at least partially surrounding, the exterior surface of the cup.

6. The vaporizer of claim 1, wherein, in response to communication of the electrical current through the heat conductor, the interior surface of the cup comprises the temperature of 250° F. to 650° F.

7. The vaporizer of claim 1, wherein the cup comprises quartz.

8. The vaporizer of claim 1, wherein the heat conductor comprises a wire.

9. The vaporizer of claim 1, wherein the interior surface of the cup comprises at least one of curved, beveled, or chamfered interior edges.

10. A vaporizer heating assembly comprising:
a heat conductor at least partially embedded within a cup, the heat conductor comprising a first end and a second end,
wherein the cup comprises an interior surface that defines a chamber,
wherein at least one of the first end and the second end is configured to receive an electrical current, and
wherein the heat conductor is configured to increase a temperature of the interior surface of the cup.

11. The vaporizer heating assembly of claim 10, wherein the heat conductor further comprises a coil embedded within a bottom side of the cup, and wherein at least one of the first end and the second end extends outwardly from an exterior surface of the cup.

12. The vaporizer heating assembly of claim 11, further comprising an electrical connector coupled to at least one of the first end and the second end.

13. The vaporizer heating assembly of claim 12, wherein the electrical connector comprises a 510 electrical thread connector.

14. The vaporizer heating assembly of claim 12, further comprising a cover coupled to, and at least partially surrounding, the exterior surface of the cup.

15. The vaporizer heating assembly of claim 10, wherein, in response to communication of the electrical current through the heat conductor, the interior surface of the cup comprises the temperature of 250° F. to 650° F.

16. The vaporizer heating assembly of claim 10, wherein the cup comprises quartz.

17. The vaporizer heating assembly of claim 10, wherein the heat conductor comprises a wire.

18. The vaporizer heating assembly of claim 10, wherein the interior surface of the cup comprises at least one of curved, beveled, or chamfered interior edges.

19. A vaporizer heating assembly, comprising:
a quartz cup comprising an interior surface and an exterior surface, wherein the interior surface comprises at least one of curved, beveled, or chamfered interior edges and the exterior surface is surrounded by a cover;
a heat conductor comprising a wire coil, a first end, and a second end, wherein the wire coil is embedded in a bottom side of the quartz cup and at least one of the first end and the second end extend outward from the exterior surface of the quartz cup; and
an electrical connector coupled to, and in electrical communication with, at least one of the first end and the second end, wherein the electrical connector is configured to communicate an electrical current from a battery to the heat conductor.

20. The vaporizer heating assembly of claim 19, wherein, in response to communication of the electrical current through the heat conductor, the interior surface of the quartz cup comprises a temperature of 250° F. to 650° F.

* * * * *